(12) United States Patent
Carroll

(10) Patent No.: US 8,609,844 B2
(45) Date of Patent: Dec. 17, 2013

(54) METHOD FOR EXTRACTING AND PURIFYING BISBENZYLISOQUINOLINES

(75) Inventor: Ron D. Carroll, Fayetteville, NY (US)

(73) Assignee: CBA Pharma, Inc., Lexington, KY (US)

( * ) Notice: Subject to any disclaimer, the term of this patent is extended or adjusted under 35 U.S.C. 154(b) by 323 days.

(21) Appl. No.: 12/939,660

(22) Filed: Nov. 4, 2010

(65) Prior Publication Data

US 2011/0105755 A1    May 5, 2011
US 2013/0231483 A2    Sep. 5, 2013

Related U.S. Application Data

(60) Provisional application No. 61/258,421, filed on Nov. 5, 2009.

(51) Int. Cl.
*C07D 491/147* (2006.01)
(52) U.S. Cl.
USPC .......................................................... 546/35
(58) Field of Classification Search
None
See application file for complete search history.

(56) References Cited

U.S. PATENT DOCUMENTS

| 5,025,020 | A | 6/1991 | Van Dyke |
| 6,218,541 | B1 | 4/2001 | Wang |
| 2005/0038271 | A1 | 2/2005 | Khachik |

FOREIGN PATENT DOCUMENTS

JP    02243627    9/1990

OTHER PUBLICATIONS

Written Opinion for PCT/US2010/55437 completed Dec. 28, 2010.*
Beijing Medical College,Beijing Chinese Traditional Medical College, Ingredient Chemistry of Chinese Herbs (for Pharmacy,Chinese Herbs Specialty), Trial Edition Textbook of Medical College and Pharmacy College, p. 132, People's Health Press 1980.

* cited by examiner

*Primary Examiner* — Zinna Northington Davis
(74) *Attorney, Agent, or Firm* — Mitchell Intellectual Property Law, PLLC

(57) ABSTRACT

A method for purifying extracted crude d-tetrandrine by dissolving the crude d-tetrandrine powder in ethanol, treating the solution with a decolorizing agent, filtering, reducing the filtered solution under heat and vacuum, cooling the solution, filtering it and drying the filtered cake to yield substantially pure d-tetrandrine.

11 Claims, No Drawings

METHOD FOR EXTRACTING AND PURIFYING BISBENZYLISOQUINOLINES

This application claims benefit of 61/258,421 filed Nov. 5, 2009.

The present invention relates to the extraction and purification of bisbenzylisoquinolines from botanical material.

SUMMARY OF THE INVENTION

In the present invention, crude d-tetrandrine extracted from *Stephania Tetrandra* and separated from other bisbenzylisoquinolines in the extraction is purified further by dissolving in ethanol, treating with a decolorizing agent, filtering, reducing, cooling, filtering and drying, to yield substantially pure d-tetrandrine. These and other objects, advantages and features of the invention will be more fully understood and appreciated by reference to the Description of the Preferred Embodiments below.

DESCRIPTION OF THE PREFERRED EMBODIMENTS

In the preferred embodiments, bisbenzylisoquinolines are preferably extracted from ground or macerated. *Stephania Tetrandra* S. Moore tuber using methanol or ethanol, concentrated to a thick oil and dried. The resulting powder is acidified, the resulting slurry filtered, and the acidified solution treated with sodium hydroxide to a pH of from about 11 to about 12. The precipitate obtained from vacuum filtration is dissolved with benzene, allowed to settle, and the benzene solution layer is decanted and concentrated to a thick oil and dried under vacuum to a solid. The solid is ground, dissolved in acetone, polish filtered to remove any fines, and then vacuum concentrated. The concentrate is filtered and the resulting powder washed in ice cold acetone and dried. This powder is then is purified further by dissolving in ethanol, treating with a decolorizing agent, filtering, reducing under heat and vacuum, cooling, filtering and drying, to yield substantially pure d-tetrandrine.

The initial extraction from the ground or macerated *Stephania Tetrandra* with methanol or ethanol is done in a vessel heated to about 50° C., with vigorous stirring for about two hours. After cooling, the resulting slurry is filtered. The methanol extract is collected. The filtered slurry is re-extracted in methanol or ethanol in a vessel heated to about 50° C., with stirring for about two hours. As above, the slurry is cooled filtered and the ethanol solution is collected. These steps are repeated three more times.

The methanol or ethanol extracts are then combined in a distillation vessel and concentrated under heat and vacuum, until the solution is a thick oil. The oil is then vacuum dried in an oven at about 60-80° C. for about eight to 12 hours. The resulting solid is ground to a powder. If one begins with 1,000 kg of *Stephania Tetrandra* S. Moore tuber dried root powder, the expected yield upon completion of this step is about 200 kg. The dried powder can be stored for up to two years prior to use in the next process step.

The extracted powder is then dissolved and slurried with water in an extraction vessel. While cooling the vessel, concentrated hydrochloric or other appropriate acid is added with vigorous stirring until the pH of the system reaches about one or less. The resulting slurry is filtered and the acidic aqueous solution is collected. The acidic solution is charged into a crystallizer and with cooling, stirred to maintain a temperature of about 25° C. Sodium hydroxide solution, preferably about fifty percent, is then slowly added until the pH of the solution reaches to from about 11 to about 12, and a thick slurry has formed. The slurry is then stirred for about one hour at about 25° C.

The slurry is then vacuum filtered and the cake is washed with water and dried at about 60-80° C. under vacuum for about six to eight hours. If one has 200 kg of powder from the first extraction step, one will have about 100 kg of dried solid following this process phase.

D-tetrandrine is then separated from fungchinoline using benzene or toluene. The resulting dried solid is charged into an extraction vessel to which benzene or toluene is added. The mixture is thoroughly stirred at room temperature for about three hours and then allowed to settle. The top benzene or toluene layer containing d-tetrandrine is decanted off to a holding tank.

This step is then repeated on the remaining wet solid four more times. The decanted benzene layers are combined and polish filtered. The resulting combined extracts are transferred to a concentration vessel. The benzene solution is concentrated under vacuum at about 60° C. to a thick oil, and then the oil is dried under vacuum at about 60-80° C. to obtain a solid. The solid is ground, and beginning with a 100 kg charge at the beginning of this step, should yield 15 kg. This step has separated d-tetrandrine from fangchinoline, which is sometimes referred to as ethylfangchinoline. The resulting powder can be stored for two years prior to use in the next process step.

The resulting benzene extracted d-tetrandrine powder is charged into a crystallizer containing either acetone or a mixture of acetone and ethyl acetate in a ratio of acetone:ethyl acetate of from about 10:1 to about 5:1. The mixture is stirred at about 50° C. until the solid is dissolved. The warm solution is polished filtered to remove any particles. The clear solution is concentrated under a vacuum at about 30-40° C. to about one-fourth the volume and is slowly cooled with stirring to about 0-10° C. The resulting solid is granulated for about one hour. It is then collected on a vacuum filter, washed with ice cold acetone and dried at about 60° C. for several hours. The weight of dried powder should now be about 8 kg, which can be stored up to two years prior to the final purification phase.

The acetone treated dried powder is charged into a vessel containing ethanol, where it is stirred slowly at about 60° C. to form a solution. Decolorizing carbon is stirred into the mixture for about one hour. The resulting slurry is filtered while still hot to remove the carbon and transfer the resulting clear solution to a clean crystallizer.

Under a vacuum at about 50-60° C., the volume of the ethanol solution is reduced by about four-fifths to five-sixths. The vacuum is broken and the solution is slowly cooled with stirring to about 0-10° C. to form a solid. The cold slurry is granulated for one to two hours and then collected by vacuum filtration. The cake is washed with ice cold ethanol.

The resulting solid is dried in vacuum at about 50-60° C. for up to 12 hours. The dried powder will be substantially pure d-tetrandrine. By "substantially pure," we mean at least about 98% pure, and containing less than one percent fangchinoline. The dry powder is now ready for use and can be stored for up to five years in sealed plastic bags.

EXAMPLES

Example 1

*Stephania Tetrandra* S. Moore tuber (root) is collected, dried and ground to small particles. This dried root powder may be stored in this state for several years prior to use in the purification process.

Operating Instructions:
1) Charge an extraction vessel with 2000 liters of methanol.
2) With stirring charge 1000 kg of dried root powder to the vessel.
3) Heat the vessel to about 50° C. and stir vigorously for about two hours.
4) After cooling, filter the slurry and collect the methanol extract.
5) Charge 2000 liters of fresh methanol to the extraction vessel and add the recovered wet solid from step 4.
6) Heat the vessel to about 50° C. and stir for about two hours.
7) Repeat steps 4-6 three more times.
8) Transfer the combined methanol extracts to a distillation vessel and using heat and vacuum concentrate the solution to a thick oil.
9) Dry the oil in a vacuum oven at 60-80° C. for about 8-12 hours.
10) The resulting solid from step 9 is ground to a powder. The expected yield is about 200 kg and the powder can be stored for up to two years prior to use in the next process step.
11) Charge about 500 liters of water to an extraction vessel. With stirring add 200 kg of the powder from step 10 to the vessel.
12) Cool the vessel and, with vigorous stirring, slowly add concentrated HCl until the pH reaches <1.
13) Filter the resulting slurry and collect the acidic aqueous solution.
14) Charge the acidic solution to a crystallizer and with cooling and stirring to maintain a temperature of about 25° C., slowly add 50% NaOH until the pH reaches 11-12 and a thick slurry has formed. Stir the slurry for one hour at about 25° C.
15) Collect the precipitate from step 14 by vacuum filtration, wash with water and dry at about 60-80° C. under vacuum for about six to 8 hours. The weight of the dry solid should be about 100 kg.
16) Charge 100 kg of the product from step 15 to an extraction vessel and add about 250 liters of benzene. Stir the mixture vigorously at room temperature for about three hours. Allow the mixture to settle and decant the top benzene layer to a holding tank.
17) Charge 250 liters of fresh benzene to the wet solid and stir vigorously for three hours at room temperature. Let the mixture settle and decant the benzene layer to the holding tank.
18) Repeat steps 16 and 17 three more times. Polish filter the combined extracts and transfer to a concentration vessel.
19) Concentrate the benzene solution under vacuum at about 60° C. to a thick oil. Dry the oil under vacuum at 60-80° C. to a solid.
20) Grind the solid from step 19 to a powder. The expected weight should be about 15 kg. Steps 16-19 selectively remove the related substance fangchinoline from d-tetrandrine. The powder can be stored for up to two years prior to use in the next process step.
21) Charge 15 kg of the powder from step 20 to a crystallizer containing about 300 liters of acetone. Stir the acetone mixture at about 50° C. until the solid is dissolved. Polish filter the warm solution to remove any particles. Concentrate the clear solution under vacuum at about 30-40° C. to about one-quarter volume and slowly cool the resulting solution with stirring to about 0-10° C. Granulate the resulting solid for one hour.
22) Collect the solid from step 21 on a vacuum filter and wash with ice cold acetone. Dry the product at about 60° C. for several hours. The weight of the dry powder should be about 8 kg. This dry powder can be stored for up to two years prior to use in the next process step.
23) Charge 8 kg of the powder from step 22 to a vessel containing about 150 liters of 95% ethanol. Stir the vessel as it is slowly heated to about 60° C. to form a solution. Next add 300 grams of decolorizing carbon and stir the mixture for one hour and filter while still hot to remove the carbon and transfer the resulting clear solution to a clean crystallizer.
24) Under vacuum at about 50-60° C. reduce the volume of the ethanol solution to about 25-30 liters. Break vacuum and slowly cool the solution with stirring to 0-10° C. to form a solid. Granulate the cold slurry for one to two hours, then collect by vacuum filtration and wash the cake with ice cold ethanol.
25) Dry the solid from step 24 in vacuum at 50-60° C. for up to 12 hours. The weight of the dry powder should be about 6 kg of d-tetrandrine at least 98% pure containing <1% of fangchinoline. The dry powder may be stored for up to five years in sealed plastic bags prior to use.

Example 2

The exact instructions for Example 1 are followed except that in steps 1-9, 95% ethanol is substituted for methanol. The final d-tetrandrine product derived after step 25 is of the same yield and quality as produced in Example 1.

Example 3

The exact instructions for Examples 1 and 2 are followed except that in steps 16-20 toluene is substituted for benzene. The d-tetrandrine product resulting from step 25 is of the same quality and yield as produced by Example 1.

Example 4

The exact instructions for Examples 1, 2 and 3 are followed except that in steps 21 and 22 a mixture of acetone and ethyl acetate may be substituted for acetone alone. The ratio of acetone:ethyl acetate may range from 10:1 to 5:1. The d-tetrandrine produced from step 25 is of the same quality and yield as produced in Example 1.

The invention claimed is:
1. A method for purifying extracted crude d-tetrandrine comprising dissolving the crude d-tetrandrine powder in ethanol, treating the solution with a decolorizing agent, filtering, reducing the filtered solution under heat and vacuum, cooling the solution, filtering it and drying the filtered cake to yield substantially pure d-tetrandrine.
2. The method of claim 1 wherein the crude d-tetrandrine powder is dissolved in the ethanol with stirring and slowly increased heat to about 60° C.; the decolorizing agent being stirred into the resulting mixture and filtered while the solution is still at about 60° C. to remove the decolorizing agent.
3. The method of claim 2 in which the filtered solution with decolorizing agent removed is heated under vacuum at about 50-60° C. to reduce the volume of the ethanol solution by from about four-fifths to about five-sixths; breaking the vacuum and slowly cooling the solution with stirring to about 0 to about 10° C. to form a solid; granulating the cold slurry for about one to two hours, and then vacuum filtering and washing the filtered cake with ice cold ethanol; and drying the resulting powder.

4. The method of claim 1 in which the crude d-tetrandrine is obtained by extracting bisbenzylisoquinolines from *Stephania Tetrandra* S. Moore tuber; separating crude d-tetrandrine from other bisbenzylisoquinolines including fangchinoline, by stirring the extract vigorously in benzene or toluene, allowing the mixture to settle and decanting the top benzene layer into a holding tank; polish filtering the benzene or toluene liquid and concentrating it under vacuum at about 60° C. to a thick oil, which is then dried under vacuum at about 60-80° C. to a solid; and grinding the resulting solid to a powder.

5. The method of claim 4 in which the benzene step is repeated several times on each settled solid following decanting of the benzene layer.

6. The method of claim 4 in which said extraction step is conducted on the dried powder from ground or macerated *Stephania Tetrandra* S. Moore tuber using methanol or ethanol in a vessel heated to about 50° C., with vigorous stirring; filtering the resulting slurry, collecting the resulting methanol or ethanol solution, concentrating it using heat and vacuum to a thick oil; drying the oil in a vacuum and grinding the resulting solid to a powder.

7. The method of claim 6 in which methanol is used for the extraction from *Stephania Tetrandra* S. Moore tuber.

8. The method of claim 7 in which ethanol is used for the extraction from *Stephania Tetrandra* S. Moore tuber.

9. The method of claim 6 in which the methanol or ethanol extracted powder is dissolved in water, and concentrated acid is added, with cooling, until the pH of the aqueous solution reaches about one or less; the resulting slurry is filtered, and the acidic aqueous solution is cooled and stirred to maintain a temperature of about 25° C.; sodium hydroxide is then added until the pH reaches 11-12 and a thick slurry is formed; the slurry is stirred for about one hour at about 25° C., vacuum filtered, and the filtered cake washed with water and dried at about 60-80° C. under a vacuum.

10. The method of claim 4 in which the crude d-tetrandrine is dissolved in acetone or a mixture of acetone and ethyl acetate in an acetone:ethyl acetate ratio range of from about 10:1 to about 5:1; polished filtering the solution and concentrating it to about one-fourth its volume; granulating the resulting solid, collecting it on a filter, washing it and drying it.

11. The method of claim 1 in which the crude d-tetrandrine is dissolved in acetone or a mixture of acetone and ethyl acetate in an acetone:ethyl acetate ratio range of from about 10:1 to about 5:1; polished filtering the solution and concentrating it to about one-fourth its volume; granulating the resulting solid, collecting it on a filter, washing it and drying it.

* * * * *